US011690875B2

(12) United States Patent
Delorme et al.

(10) Patent No.: US 11,690,875 B2
(45) Date of Patent: Jul. 4, 2023

(54) METHOD FOR STERILISING A PLATELET LYSATE

(71) Applicant: Maco Pharma, Mouvaux (FR)

(72) Inventors: Bruno Delorme, Marcq-en-Baroeul (FR); Sabrina Viau, Wasquehal (FR); Francis Goudaliez, Faches-Thumesnil (FR)

(73) Assignee: Maco Pharma, Mouvaux (FR)

(*) Notice: Subject to any disclaimer, the term of this patent is extended or adjusted under 35 U.S.C. 154(b) by 304 days.

(21) Appl. No.: 17/179,812

(22) Filed: Feb. 19, 2021

(65) Prior Publication Data
US 2021/0196758 A1 Jul. 1, 2021

Related U.S. Application Data

(63) Continuation of application No. 15/577,993, filed as application No. PCT/FR2016/051265 on May 27, 2016, now Pat. No. 10,946,046.

(30) Foreign Application Priority Data

May 29, 2015 (FR) ...................................... 1554883

(51) Int. Cl.
C12N 5/078 (2010.01)
A61K 35/19 (2015.01)
(Continued)

(52) U.S. Cl.
CPC ............ A61K 35/19 (2013.01); A61L 2/0035 (2013.01); C12N 5/0644 (2013.01);
(Continued)

(58) Field of Classification Search
CPC ...... A61K 35/19; A61L 2/0035; C12N 5/0644
See application file for complete search history.

(56) References Cited

U.S. PATENT DOCUMENTS 8,835,104 B2  9/2014 Mayaudon et al.
2011/0171731 A1  7/2011 Dietz et al.
(Continued)

FOREIGN PATENT DOCUMENTS

WO  0033893 A1  6/2000
WO  0170279 A1  9/2001
(Continued)

OTHER PUBLICATIONS

Azouna, N. Ben, et al. "Phenotypical and functional characteristics of mesenchymal stem cells from bone marrow: comparison of culture using different media supplemented with human platelet lysate or fetal bovine serum." Stem Cell Res Ther 3.1 (2012): 6.
(Continued)

Primary Examiner — Blaine Lankford
Assistant Examiner — Lauren K Van Buren
(74) Attorney, Agent, or Firm — Bachman & LaPointe, P.C.

(57) ABSTRACT

A method for sterilising a platelet lysate in the liquid state comprising at least the endogenous growth factors TGF-beta 1, EGF, PDGF-AB, IGF-1, VEGF and bFGF. The method comprising freezing the liquid platelet lysate in order to obtain a frozen platelet lysate, and irradiating the frozen platelet lysate with ionising radiation in order to obtain a sterilised platelet lysate, the irradiation being adapted so as to preserve at least 80% of the concentration of at least one of the endogenous growth factors chosen from the group consisting of TGF-beta 1, EGF, PDGF-AB, IGF-1 and VEGF.

7 Claims, 2 Drawing Sheets

(51) Int. Cl.
A61L 2/00 (2006.01)
C12N 5/0775 (2010.01)
(52) U.S. Cl.
CPC ........ *C12N 5/0662* (2013.01); *C12N 2500/84* (2013.01); *C12N 2501/115* (2013.01); *C12N 2529/00* (2013.01)

(56) References Cited

U.S. PATENT DOCUMENTS

| | | |
|---|---|---|
| 2012/0156306 A1 | 6/2012 | Weissman et al. |
| 2012/0252001 A1 | 11/2012 | Shaz et al. |
| 2012/0315698 A1 | 12/2012 | Harmon et al. |
| 2014/0056989 A1 | 2/2014 | Weissman et al. |

FOREIGN PATENT DOCUMENTS

| | | |
|---|---|---|
| WO | 2010033605 A2 | 3/2010 |
| WO | 2011148326 A1 | 12/2011 |
| WO | 2013042095 A1 | 3/2013 |
| WO | 2014076200 A1 | 5/2014 |

OTHER PUBLICATIONS

Castiglia, Sara, et al. "Inactivated human platelet lysate with psoralen: a new perspective for mesenchymal stromal cell production in Good Manufacturing Practice conditions." Cytotherapy 16.6 (2014): 750-763.

Pérez-Ilzarbe, Maitane, et al. "Comparison of ex vivo expansion culture conditions of mesenchymal stem cells for human cell therapy." Transfusion 49.9 (2009): 1901-1910.

Viau et al.: "Poster 139: Preservation of Quality and Efficacy of Human Platelet Lysate Pathogen Reduced With Photosensitizing Additive-Free Theraflex UV-Platelets Technolgy", Apr. 27, 2015, XP055257770, http://www.sciencedirect.com.

Natalie Fekete et al.: "Platelet lysate from whole blood-derived pooled platelet concentrates and apheresis-derived platelet concentrates for the isolation and expansion of human bone marrow mesenchymal stromal cells: production process, content and identification of active components", Cytotherapy, vol. 14, No. 5, May 1, 2012, pp. 540-554, XPO55178087, ISSN: 1465-3249, DOI: 10.3109/14653249.2012.655420.

Daniel Tzu-Bi Shih et al.: "Preparation, quality criteria, and properties of human blood platelet lysate supplements for ex vivo stem cell expansion", New Biotechnology, vol. 32, No. 1, Jan. 1, 2015, pp. 199-211, XPO55258280, NL, ISSN: 1871-6784, DOI: 10.1016/j.nbt.2014.06.001.

International Search Report for PCT/FR2016/051265 dated Aug. 9, 2016.

V.S. Hornsey et al., Extended storage of platelets in SSP+ platelet additive solution, Vox Sanguinis (2006) vol. 91, pp. 41-46, © 2006 Blackwell Publishing, DOI: 10.1111/j.1423-0410.2006.00771.x.

METHOD FOR STERILISING A PLATELET LYSATE

CROSS-REFERENCE TO RELATED APPLICATIONS

The instant application is a continuation of U.S. patent application Ser. No. 15/577,993, filed Nov. 29, 2017, which is a 371 of international application no. PCT/FR2016/051265, filed May 27, 2016, which claims priority of FR 1554883, filed May 29, 2015.

BACKGROUND

The invention relates to a method for sterilising a platelet lysate as well as a sterilised platelet lysate obtained using such a method and a cell culture method using such a sterilised platelet lysate.

The invention applies to the field of blood platelet-derived products, and particularly to the field of cell culture for culturing cells for therapeutic use, more particularly mesenchymal stem cells.

In order to culture animal cells in vitro, base media such as RPMI (Roswell Park Memorial Institute), MEM (Modified Eagle Medium) or DMEM (Dulbecco Modified Eagle Medium) essentially comprising mineral salts, glucose, amino acids, vitamins and nitrogenous bases are conventionally used. These media are generally supplemented extemporaneously with antibiotics to prevent bacterial contamination, L-glutamine, an unstable amino acid, and between 1.5 and 10% foetal bovine serum as a nutrient supplement.

However, foetal bovine serum is a potential carrier of xenogenous pathogenic agents. In particular, when the serum is of bovine origin, the risk of contamination with prions or viruses is not null.

To remedy these drawbacks, it has been proposed to replace the serum by human platelet lysate which has the advantage of comprising a large quantity of growth factors of human origin such as for example Transforming Growth Factor-beta1 (TGF-beta1), Epidermal Growth Factor (EGF), Platelet-Derived Growth Factor-AB (PDGF-AB), Insulin-like Growth Factor-1 (IGF-1), Vascular Endothelial Growth Factor (VEGF) and Fibroblast Growth Factor 2 (FGF-2), also known as Basic Fibroblast Growth Factor (bFGF).

A superior proliferation rate of mesenchymal stem cells cultured in a base medium supplemented with human platelet lysate compared to a reference medium comprising the same base medium supplemented with foetal bovine serum (FBS) and supplemented with 1 ng/ml of FGF-2 has thus been demonstrated (Azouna, N. Ben, et al. "Phenotypical and functional characteristics of mesenchymal stem cells from bone marrow: comparison of culture using different media supplemented with human platelet lysate or fetal bovine serum." Stem Cell Res Ther 3.1 (2012): 6).

However, the platelet lysate being of human origin, it also presents a pathogenic contamination risk which needs to be taken into account and minimised. Indeed, platelet lysates may be potential carriers of viruses, bacteria or protozoa.

As such, there is a real need to develop safer platelet lysates for cell culture.

The document WO 2013/042095 and the article by S. Castiglia (Castiglia, Sara, et al. "Inactivated human platelet lysate with psoralen: a new perspective for mesenchymal stromal cell production in Good Manufacturing Practice conditions." Cytotherapy 16.6 (2014): 750-763) disclose a platelet lysate obtained from buffy coat-derived platelet concentrates which have undergone viral inactivation by ultraviolet radiation in the present of psoralen. However, this viral inactivation technique has the drawback of having to use an additional molecule which subsequently needs to be removed from the treated product.

The document WO 2010/033605 proposes passing the platelet lysate through a 0.45 µm or 0.22 µm filter. However, such filters are not suitable for removing the small viruses optionally present.

The document WO 2011/148326 proposes preparing a virally inactivated platelet lysate by treating a platelet concentrate with a solvent/detergent. However, the chromatographic method used for removing the solvent/detergent from the lysate thereby obtained, results in the removal in particular of the growth factors VEGF and PDGF.

In an alternative embodiment described in the document US 2012/0156306, the platelet lysate treated with solvent/detergent subsequently undergoes a second viral inactivation treatment chosen from pasteurisation, nano-filtration, low-pH treatment, ultraviolet irradiation or sodium thiocyanate treatment.

In the case of proteins, the document WO 01/70279 teaches that gamma ray irradiation must be carried out on proteins free from residual solvent, i.e. in a freeze-dried form, and/or in the presence of a stabiliser so as not to denature same.

However, freeze-drying is a batch process which results in multiple procedures and relatively significant treatment times which thereby increase the costs associated with the use of such processes. Adding a stabiliser also represents an additional step and compound in the treatment of the product which it would be advantageous to do away with.

Furthermore, even in freeze-dried form, some growth factors do not withstand gamma irradiation. For example, the document WO 00/33893 shows a loss of activity of more than 90% of the freeze-dried growth factor PDGF sterilised by gamma irradiation compared to non-sterilised freeze-dried PDGF.

Finally, the document WO 2014/076200 describes culture supplements based on platelet-enriched or depleted plasma fractions. It is indicated that such culture supplements may be frozen, freeze-dried, sterilised by gamma irradiation at a dose of 1 kGy and stored at −20° C. This relatively low irradiation dose is not sufficient to inactivate viruses and bacteria.

Unexpectedly and contrary to the teaching of the prior art documents, it was observed that a platelet lysate having been subjected, in a frozen state, to a high gamma ray irradiation dose retains a satisfactory biological activity without requiring freeze-drying or a stabiliser.

Moreover, while adding exogenous bFGF to non-irradiated platelet lysate has no effect on the cell proliferation rate (Pérez-Ilzarbe, Maitane, et al. "Comparison of ex vivo expansion culture conditions of mesenchymal stem cells for human cell therapy." Transfusion 49.9 (2009): 1901-1910), platelet lysate irradiated in the frozen state with gamma radiation exhibits the novel property of increasing the cell proliferation rate in the presence of exogenous bFGF.

SUMMARY OF THE INVENTION

As such, according to a first aspect, the invention relates to a method for sterilising a platelet lysate in the liquid state comprising at least the endogenous growth factors TGF-beta1, EGF, PDGF-AB, IGF-1, VEGF and bFGF, said method comprising:

freezing said liquid platelet lysate in order to obtain a frozen platelet lysate, irradiating said frozen platelet lysate with ionising radiation in order to obtain a sterilised platelet lysate, said irradiation being adapted so as to preserve at least 80% of the concentration of at least one of the endogenous growth factors chosen from the group consisting of TGF-beta1, EGF, PDGF-AB, IGF-1 and VEGF.

According to a second aspect, the invention relates to the sterilised platelet lysate obtained with the method according to the first aspect of the invention.

According to a third aspect, the invention relates to a method for culturing cells, particularly mesenchymal stem cells, comprising contacting said cells with a nutrient composition comprising a base medium and a sterilised platelet lysate according to the second aspect of the invention.

Further aims and advantages will emerge in the course of the following description.

DETAILED DESCRIPTION

Figure 1:
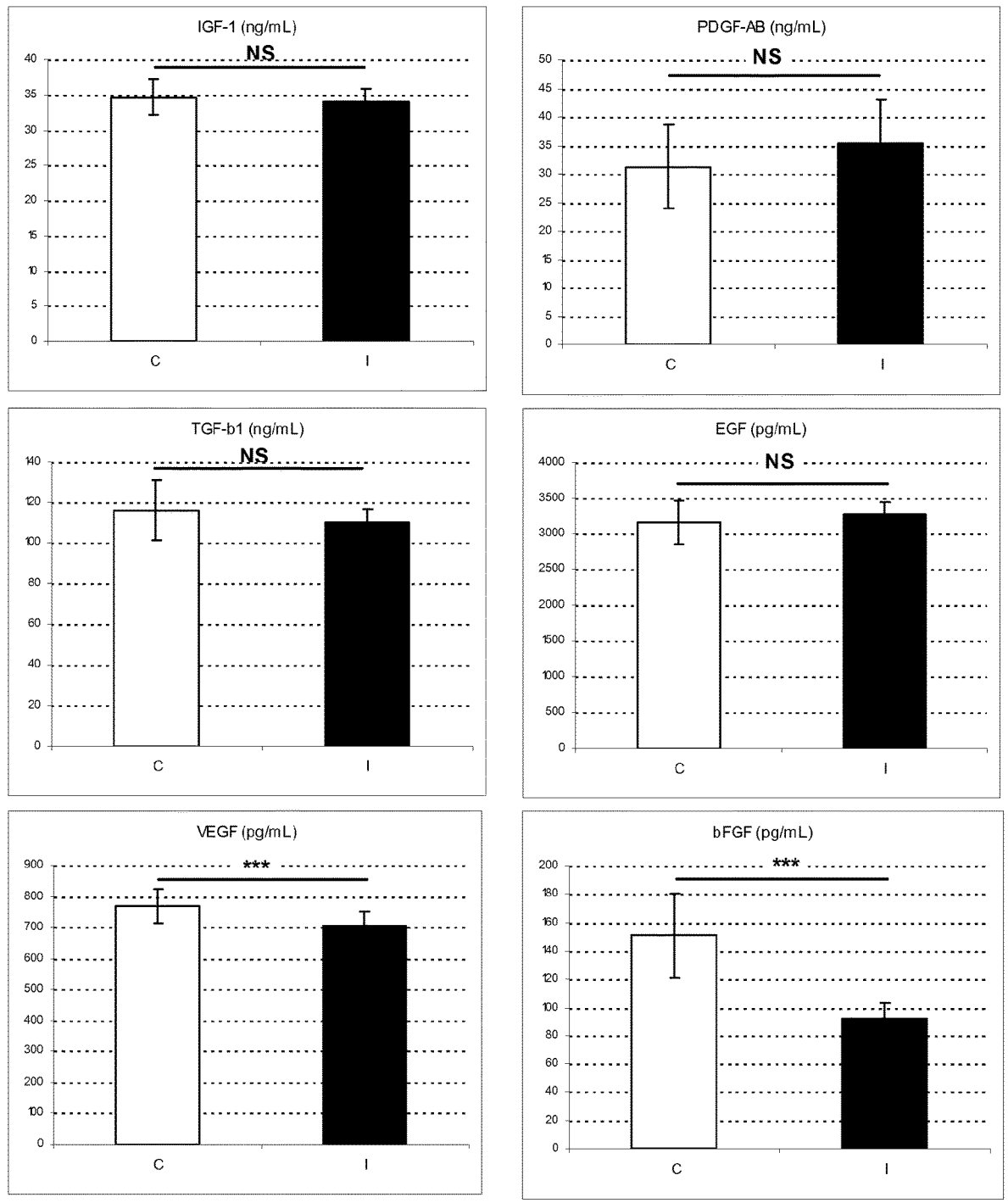
FIG. 1 represents the mean concentrations of the growth factors IGF-1, PDGF-AB, TGF-beta1, EGF, VEGF and bFGF in non-irradiated platelet lysates (C) and in platelet lysates sterilised using the method according to the invention (I).

The invention relates to a method for sterilising a platelet lysate with a view to obtaining a sterilised platelet lysate.

The term sterilisation method denotes a method for reducing and/or inactivating pathogens including viruses, bacteria, fungi and bacterial spores.

The term platelet lysate denotes the platelet lysis product, i.e. the product obtained after disintegration of the cell membrane which gives rise to the release of the molecules (growth factors, cytokines) normally contained inside the platelets.

As such, the platelet lysate particularly comprises a concentrate of growth factors including IGF-1, PDGF-AB, TGF-beta1, EGF, VEGF and bFGF. Further growth factors present in the platelet lysate are particularly Connective Tissue Growth Factor (CTGF) and Stromal Cell-Derived Factor-1alpha (SDF-1alpha). These growth factors are said to be endogenous.

The term endogenous substance denotes any substance produced by the platelets or contained in the initial platelet suspension used to prepare the platelet lysate, as opposed to an exogenous substance introduced into the platelet lysate or into the initial platelet suspension.

Platelet lysis is for example carried out with one or a plurality of freezing/thawing cycles, using ultrasound or with a solvent/detergent treatment.

In the sterilisation method described, the platelet lysate is obtained from animal, particularly human, platelets obtained from an apheresis method or prepared from a blood donation.

According to a first aspect of the invention, the method for sterilising a platelet lysate is carried out using a platelet lysate in the liquid state, said platelet lysate comprising at least the endogenous growth factors IGF-1, PDGF-AB, TGF-beta1, EGF, VEGF and bFGF, said method comprising:

freezing said liquid platelet lysate in order to obtain a frozen platelet lysate, irradiating said frozen platelet lysate with ionising radiation in order to obtain a sterilised platelet lysate, said irradiation being adapted so as to preserve at least 80% of the concentration of at least one of the endogenous growth factors chosen from the group consisting of TGF-beta1, EGF, PDGF-AB, IGF-1 and VEGF.

The platelet lysate in the liquid state is obtained from a platelet suspension. The platelet suspension is particularly a platelet concentrate or a mixture of platelet concentrates, a leuco-platelet layer, also known as buffy coat, or a mixture of leuco-platelet layers, a platelet-enriched plasma or a platelet-enriched plasma mixture.

More particularly, the platelet suspension is a platelet concentrate obtained from apheresis or prepared from a blood donation or a mixture of platelet concentrates obtained from apheresis or prepared from blood donations. For example, the mixture comprises between 2 and 7 platelet concentrates, in particular between 3 and 5 platelet concentrates.

The platelet concentrate is either fresh, i.e. suitable for transfusion to a patient, or expired, i.e. stored for 5 days of more after the preparation thereof and no longer suitable for transfusion to a patient.

The platelet suspension comprises platelets in suspension in a liquid medium comprising plasma.

For example, the liquid medium only comprises plasma. According to a further example, the liquid medium further comprises a platelet preservation solution such as SSP+ solution (Maco Pharma) or Intersol® (Fenwall).

In one particular example, the liquid medium comprises from 20% to 100%, particularly 30% plasma and from 0% to 80%, particularly 70% platelet preservation solution.

In order to furnish, i.e. make available, the platelet lysate in the liquid state, the sterilisation method comprises the preliminary preparation of the platelet lysate in the liquid state from a platelet suspension.

According to a particular embodiment, the preliminary preparation of said platelet lysate in the liquid state from a platelet suspension comprises the following successive steps:

subjecting said platelet suspension to at least one freezing/thawing cycle so as to obtain a lysed platelet composition, separating said lysed platelet composition into a clear platelet lysate fraction and a cellular debris fraction, isolating said platelet lysate in the liquid state.

The platelet suspension is subjected to at least one freezing/thawing cycle. In particular, 2 to 3 freezing/thawing cycles are performed.

The platelet suspension is first frozen at a temperature between −10° C. and −80° C., particularly −80° C. Freezing lasts at least 24 hours. Then, the platelet suspension is thawed at a temperature ranging from 4° C. to 37° C., particularly at ambient temperature or at 4° C.

The freezing/thawing step induces the destruction of the platelets with the release of the content thereof, and particularly of the endogenous factors thereof.

After the freezing/thawing cycle, a lysed platelet composition comprising the platelet content, the liquid medium wherein the platelets were suspended and the cellular debris is obtained.

Said lysed platelet composition is then separated into a clear platelet lysate fraction and a cellular debris fraction.

According to one particular embodiment, this separation is performed by centrifuging said lysed platelet composition so as to obtain a platelet lysate supernatant and a cellular debris sediment.

Alternatively, the separation is performed by filtration so as to obtain a platelet lysate filtrate and a cellular debris retentate.

The platelet lysate in the liquid state is finally isolated by extraction. This platelet lysate comprises at least the endogenous growth factors IGF-1, PDGF-AB, TGF-beta1, EGF, VEGF and bFGF.

The initial platelet suspension comprising plasma, the sterilised platelet lysate according to the invention also comprises plasma, and particularly plasma constituents such as fibrinogen, globulin, albumin, triglycerides, interleukins and interferons.

Once the platelet lysate in the liquid state has been prepared, the method according to the invention comprises freezing said liquid platelet lysate in order to obtain a frozen platelet lysate.

The freezing of the liquid platelet lysate is carried out at a temperature between −10° C. and −80° C., particularly approximately −80° C.

The platelet lysate is packaged in a freezing-resistant container and particularly in a bag. The freezing-resistant material is particularly ethylene-vinyl acetate, polyethylene or a fluoropolymer such as fluorinated ethylene propylene.

In order to carry out the sterilisation, the platelet lysate in its frozen state is subsequently subjected to irradiation with ionising radiation. The platelet lysate is irradiated in a non-freeze-dried state, i.e. it comprises water.

According to one embodiment, the ionising radiation is gamma radiation.

Gamma radiation is electromagnetic radiation composed of high-energy photons, of the order of 1.6 MeV. It is for example emitted by a source of cobalt 60.

This ionising radiation induces the destruction of microorganisms by rupturing the deoxyribonucleic acid (DNA) chain or the ribonucleic acid (RNA) strand, thereby enabling the inactivation of bacteria and viruses, for example.

However, ionising radiation is liable to damage polymers by creating ions which are converted into active free radicals and which, by recombining, create new permanent chemical bonds.

According to the invention, the irradiation with ionising radiation is adapted so as to preserve at least 80% of the concentration of at least one of the endogenous growth factors chosen from the group consisting of TGF-beta1, EGF, PDGF-AB, IGF-1 and VEGF.

In particular, the irradiation with gamma radiation is adapted so as to preserve at least 80%, particularly at least 90% of the concentration of each of the growth factors TGF-beta1, EGF, PDGF-AB, IGF-1 and VEGF.

Even more particularly, the irradiated platelet lysate according to the invention preserves at least 95% of the concentration of each of the growth factors TGF-beta1, EGF, PDGF-AB and IGF-1.

The growth factors IGF, PDGF, TGF-beta1 and EGF, and VEGF are the main growth factors present in the platelet lysate. Furthermore, the growth factors PDGF, bFGF, TGF-beta1 are of importance for the proliferation of cells, particularly mesenchymal stem cells. Maintaining the concentration thereof in the sterilised platelet lysate is therefore an indicator of maintenance of the biological activity of the platelet lysate, particularly in terms of cell proliferation.

As such, the amplification rate of mesenchymal stem cells in a nutrient composition comprising a base medium and a platelet lysate sterilised with the method according to the invention is preserved to at least 80%, particularly to at least 85% with respect to the amplification rate of mesenchymal stem cells in a nutrient composition comprising a base medium and a platelet lysate not sterilised with the method according to the invention.

The term base medium denotes a medium intended for cell culture such as RPMI, MEM, DMEM medium or a mixture of these media. These base media essentially comprise mineral salts, glucose, amino acids, vitamins and nitrogenous bases.

The platelet lysate sterilised with the method according to the invention thereby retains efficacy in terms of mesenchymal stem cell proliferation.

According to one embodiment, the irradiation is carried out at an absorbed dose within the range from 20 kGy to 60 kGy, particularly from 35 kGy to 45 kGy.

The absorbed dose is the quantity of energy communicated to the material per unit of mass.

For example, irradiation is performed for a duration within the range from 600 seconds to 1800 seconds, preferentially from 900 Seconds to 1200 seconds, and more preferentially for 1075 seconds, with a source having an activity of 1 Mci ($3.7 \times 10^{19}$ Bq).

In practice, irradiation with ionising radiation of the frozen platelet lysate is carried out at a low temperature, the frozen platelet lysate being placed in dry ice.

Advantageously, the irradiation step is carried out on the platelet lysate in the final packaging thereof, particularly in a bag. The bag is for example made of a material resistant to irradiation with ionising radiation such as ethylene-vinyl acetate.

Under these irradiation conditions, particularly in respect of relatively high dose enabling the destruction of pathogens and of very low temperature, it is observed surprisingly that the concentration of most of the growth factors contained in the platelet lysate remains substantially equivalent. This is the case for the growth factors TGF-beta1, EGF, PDGF-AB, IGF-1, and to a lesser degree VEGF.

Only the concentration of the growth factor bFGF undergoes a more pronounced reduction, of the order of 40%.

Moreover, it should be noted that the irradiation with ionising radiation is in particular carried out with no exogenous stabilising compound, known to reduce damage to the material to be irradiated with ionising radiation. Examples of stabilising compounds are antioxidants (ascorbic acid, tocopherol), free radical trapping agents, certain polysaccharides such as cellulose or chitosan, and certain proteins such as gelatine.

According to one particular embodiment, the method according to the invention further comprises a step for filtering the platelet lysate in the liquid state through a filter of 0.65 µm porosity or less, particularly 0.95 µm or less, and especially 0.22 µm or less.

The filtration step is for example carried out at the end of the preliminary preparation of the platelet lysate in the liquid state, prior to the freezing thereof with a view to irradiation.

When the platelet lysate is filtered through a filter having a porosity of 0.22 μm or less, the filter is described as sterilising in that it retains particularly bacteria greater than 0.22 μm in size.

In this case, the platelet lysate undergoes two sterilisation processes: sterilising filtration and sterilisation with ionising radiation, which makes it possible to broaden the spectrum of eliminated and/or inactivated pathogens potentially present in the platelet lysate.

In particular, the sterilised platelet lysate according to the invention is packaged in a bag, particularly made of ethylene-vinyl acetate.

According to a further aspect, the invention relates to a sterilised platelet lysate obtained with the method according to the first aspect of the invention.

The platelet lysate prepared according to the sterilisation method according to the invention has a particular growth factor profile.

For example, the sterilised platelet lysate according to the invention comprises a concentration of the endogenous growth factor bFGF less than 120 pg/ml, particularly less than 100 pg/ml. The concentration of endogenous IGF-1 is between 30 and 90 ng/ml. The concentration of endogenous PDGF-AB is between 20 and 45 ng/ml. The concentration of endogenous TGF-beta1 is between 100 and 130 ng/ml. The concentration of endogenous EGF is between 2500 and 3700 ng/ml. The concentration of endogenous VEGF is between 600 and 800 pg/ml, particularly between 600 and 700 pg/ml.

The sterilised platelet lysate according to the invention also comprises plasma constituents such as fibrinogen, globulins, albumin, triglycerides, interleukins and interferons, the quantity whereof varies according to the starting product of the platelet lysate, particularly according to whether the platelet suspension comprises a platelet preservation solution or not.

For example, the endogenous fibrinogen concentration in a sterilised platelet lysate according to the invention prepared from a platelet suspension comprising 30% plasma and 70% of a platelet preservation solution is less than 0.4 g/l, i.e. a loss of approximately 20% with respect to a platelet lysate not irradiated with gamma radiation.

According to a further example, the endogenous fibrinogen concentration in a sterilised platelet lysate according to the invention prepared from a platelet suspension comprising 100% plasma is less than 1 g/l, particularly less than 0.70 g/l and more particularly less than 0.60 g/l, i.e. a loss of endogenous fibrinogen varying from more than 25% to more than 45%.

Advantageously, the platelet lysate according to the invention is devoid of exogenous substances. Such substances are particularly (i) stabilisers such as antioxidants (ascorbic acid, tocopherol), free radical trapping agents, certain polysaccharides such as cellulose or chitosan, and certain proteins such as gelatine, and peptides or dipeptides such as glycine or alanylglutamine; (ii) exogenous molecules capable of binding platelet-derived factors, such as heparin or dextran sulphate; (iii) amphiphilic polymers such as polyvinylpyrrolidone or cellulose derivatives.

Moreover, the sterilised platelet lysate according to the invention has the advantage of having reduced coagulation properties with respect to a platelet lysate not sterilised with the method according to the invention.

Indeed, the conventional method for preparing the platelet lysate with freezing/thawing results in a platelet lysate comprising fibrinogen, a soluble protein present in plasma and involved in coagulation.

When the conventionally prepared platelet lysate is contacted with a base medium comprising calcium, the medium coagulates or "gels". To prevent this coagulation, it is necessary to add an anticoagulant such as heparin to the base medium.

Surprisingly and particularly advantageously, the platelet lysate obtained with the sterilisation method does not coagulate when it is added to the culture medium, particularly when the quantity of platelet lysate added to the culture medium is within the range from 1% to 15%, particularly from 2% to 10%, even more particularly from 2% and 5%. Adding heparin is then no longer necessary.

Even more unexpectedly, the sterilised platelet lysate according to the invention has very specific properties in relation to cell proliferation, particularly of mesenchymal stem cells.

Indeed, supplementing a base medium with a sterilised platelet lysate according to the invention and the exogenous growth factor bFGF induces a beneficial effect on mesenchymal stem cell proliferation, whereas adding exogenous bFGF to a base medium supplemented with platelet lysate not irradiated with ionising radiation has no effect on this proliferation.

Therefore, there is a synergistic effect between the addition of exogenous bFGF and irradiation with ionising radiation of a platelet lysate.

As such, according to a third aspect, the invention relates to a method for culturing cells, particularly mesenchymal stem cells, comprising contacting said cells with a nutrient composition comprising a base medium and a sterilised platelet lysate according to the second aspect of the invention.

The mesenchymal stem cells are for example human mesenchymal stem cells obtained from bone marrow or from umbilical cord blood.

According to one particular embodiment, the nutrient composition comprises from 2% to 25%, in particular from 5% to 15%, and even more particularly from 8 to 10% of sterilised platelet lysate according to the invention.

In particular, the sterilised platelet lysate is added extemporaneously in a preliminary fashion to said base medium so as to form said nutrient composition.

As the irradiated platelet lysate has a reduced coagulation power, it is not necessary to add to the nutrient composition an anticoagulant such as heparin to prevent the coagulation thereof and keep same in a liquid state. As such, according to one embodiment of the method for culturing cells, the nutrient composition is in liquid form and free from anticoagulant.

Advantageously, the method for culturing cells further comprises the extemporaneous addition to said nutrient composition of exogenous bFGF.

In particular, the concentration of exogenous bFGF added is within the range from 0.1 ng/ml to 15 ng/ml, particularly from 0.1 to 1.5 ng/ml, for example 1 ng/ml.

Example

Preparation of a Platelet Lysate

A batch of platelet lysate is prepared as described below.

Platelet concentrates comprising 70% Intersol® preservation solution and 30% plasma were prepared from a pool of five buffy coats and stored in a storage bag.

The storage bags were frozen at −80° C. for a period of approximately 24 hours before being thawed at ambient temperature for approximately 24 hours.

The thawed storage bags are then centrifuged at a speed of 5000 g for 10 minutes so as to separate the supernatant comprising the platelet lysate from the sediment comprising the cellular debris. The supernatant from each of the storage bags is transferred into a mixing bag so as to obtain a platelet lysate mixture. The platelet lysate mixture is then redistributed into small 50 ml bags made of ethylene-vinyl acetate.

A further batch of platelet lysate is prepared in a similar fashion, with the exception that the platelet lysate mixture is filtered through a sterilising filter of 0.22 µm porosity before being redistributed into small bags made of ethylene vinyl acetate.

The small bags are then frozen at −80° C. for storage.

Irradiation of Platelet Lysates

The frozen small bags containing the platelet lysate are irradiated with gamma radiation at an absorbed dose of 35 kGy or 45 kGy.

Assay of Growth Factors

The growth factors IGF1, PDGF-AB, TGF-beta1, EGF, VEGF and bFGF are assayed in samples from the two batches of platelet lysate (filtered and non-filtered), the samples having been irradiated with gamma radiation at 35 kGy and at 45 kGy or not irradiated. Three assays are performed for each sample.

The assays of the growth factors are performed using ELISA Quantikine commercial kits supplied by Bio-Techne (references DG100 for human IGF-1, DHD00C for human PDGF-Ab, DB100B for human TGF-beta1, DEG00 for human EGF, DVE00 for human VEGF, and DFB50 for human FRG) according to the manufacturer's instructions.

FIG. 1 represents the mean concentrations of the growth factors IGF-1, PDGF-AB, TGF-beta1, EGF, VEGF and bFGF in non-irradiated platelet lysates (C), filtered or not, and in the samples irradiated with gamma radiation (I) at 35 kGy or 45 kGy, filtered or not.

The results demonstrate that irradiation with gamma radiation does not have a significant effect on the concentrations of the growth factors IGF-1, PDGF-AB, TGF-beta1 and EGF. Irradiation with gamma radiation has a moderate impact on the concentration of VEGF (−8%), and more pronounced on bFGF (−39%).

Assay of Plasma Components

Biochemical tests were carried out on a platelet lysate prepared according to example 1 in order to determine the concentration of certain components.

Fibrinogen was assayed according to the Clauss method (chronometric assay with excess thrombin).

D-dimers were assayed by latex-enhanced immunoturbidimetry (photometric reading).

Vitamin B12 and vitamin D were assayed with a chemiluminescent microparticle immunoassay (CMIA) method.

Total cholesterol was assayed by enzymatic colorimetry with cholesterol esterase/oxidase.

Sodium and chlorine were assayed by indirect selective potentiometry (specific electrode).

Colorimetry was used for the assay of total proteins (Biuret), albumin (bromocresol green), calcium (Arsenazo III) and serum iron (ferene without deproteinisation).

Mycoplasms were detected by culture on selective medium (agar).

The table below shows that, with the exception of fibrinogen, the other components tested are not impacted by gamma irradiation at doses varying from 5 to 55 kGy.

| Platelet lysate | Control | 5 KGy | 15 KGy | 35 KGy | 55 KGy |
| --- | --- | --- | --- | --- | --- |
| Fibrinogen (g/l) | 0.50 | 0.42 | 0.40 | 0.40 | <0.4 |
| D-Dimers (mg/ml) | 0.27 | 0.27 | 0.27 | 0.27 | 0.31 |
| Vitamin B12 (pg/ml) | 144 | 119 | 135 | 134 | 138 |
| Vitamin D (ng/ml) | 5.5 | 5.1 | 4.9 | 5.4 | 5.4 |
| Total cholesterol (g/l) | 0.49 | 0.49 | 0.48 | 0.47 | 0.49 |
| Sodium (mEq/l) | 182 | 182 | 180 | 181 | 181 |
| Chlorine (mEq/l) | 78 | 79 | 79 | 79 | 79 |
| Total proteins (g/l) | 18 | 18 | 18 | 18 | 18 |
| Albumin (g/l) | 12 | 12 | 12 | 12 | 12 |
| Calcium (mg/l) | 31 | 31 | 31 | 31 | 31 |
| Corrected calcium (mg/l) | 53 | 53 | 53 | 53 | 53 |
| Serum iron (µg/dl) | 30 | 30 | 31 | 30 | 31 |
| Mycoplasm ($10^3$ CFU/ml) | negative | negative | negative | negative | negative |

The same assays were performed on a platelet lysate obtained according to the method of example 1, except that the initial platelet concentrates do not comprise platelet preservation solution (100% plasma).

| Platelet lysate | Control | 5 KGy | 15 KGy | 35 KGy | 55 KGy |
| --- | --- | --- | --- | --- | --- |
| Fibrinogen (g/l) | 1.34 | 0.92 | 0.69 | 0.51 | 0.4 |

Proliferation of Mesenchymal Stem Cells

Human mesenchymal stem cells from bone marrow were cultured (4000 cells/cm$^2$) for 7 days in a nutrient composition comprising the base medium alpha-DMEM supplemented with 8% platelet lysate, filtered or not, irradiated with gamma radiation at 35 kGy, 45 kGy or not.

It was firstly observed that the step for irradiating the platelet lysate with gamma radiation induces a loss of coagulation property when placed in the presence of the base medium, rendering the addition of heparin to the medium not necessary.

In comparison, human mesenchymal stem cells from bone marrow were cultured in a nutrient composition comprising the base medium alpha-DMEM supplemented with 10% foetal bovine serum.

Figure 2:
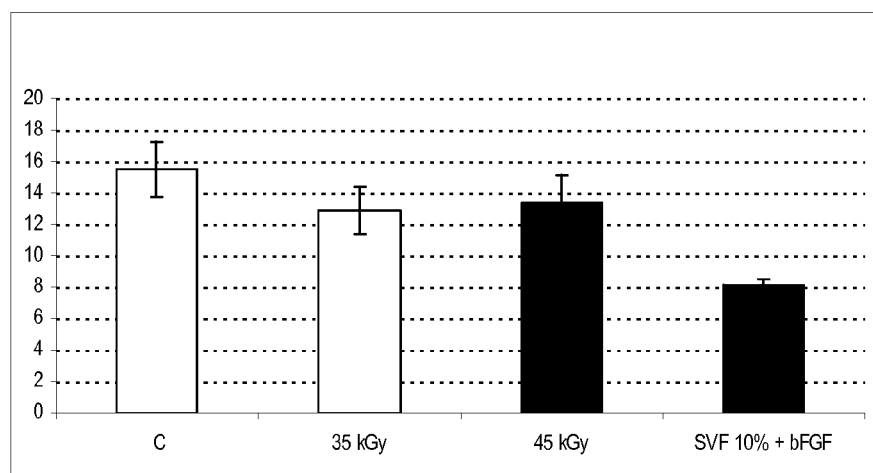
FIG. 2 shows the mean amplification rates of mesenchymal stem cells cultured in the presence of non-irradiated platelet lysates (C), platelet lysates sterilised in the frozen state with gamma irradiation at 35 kGy, platelet lysates sterilised in the frozen state with gamma irradiation at 45 kGy and foetal bovine serum supplemented with bFGF.

FIG. 2 shows the mean amplification factors of mesenchymal stem cells cultured with non-irradiated platelet lysate (C), filtered or not, and irradiated with gamma radiation at 35 kGy or at 45 kGy, filtered or not; and in comparison with cells cultured with foetal bovine serum and bFGF.

The mean reduction of the amplification factor is of the order of 15%.

Effect of bFGF Growth Factor

The growth factor bFGF is known to stimulate the proliferation of numerous cell types. However, when the mesenchymal stem cell culture is produced with platelet lysate as a replacement of foetal bovine serum, the effect of exogenous bFGF on the cellular amplification rate is negligible.

The effect on the proliferation of mesenchymal stem cells of adding exogenous bFGF (1 ng/ml) to a base medium supplemented with platelet lysate irradiated (8%) with gamma radiation (I) or non irradiated (C) was tested.

By way of comparison, the effect on the proliferation of mesenchymal stem cells of adding exogenous bFGF (1 ng/ml) to a base medium supplemented with foetal bovine serum (10%) of research grade (SVF (RG)) or of clinical grade (SVF (CG)) was also tested.

Figure 3:
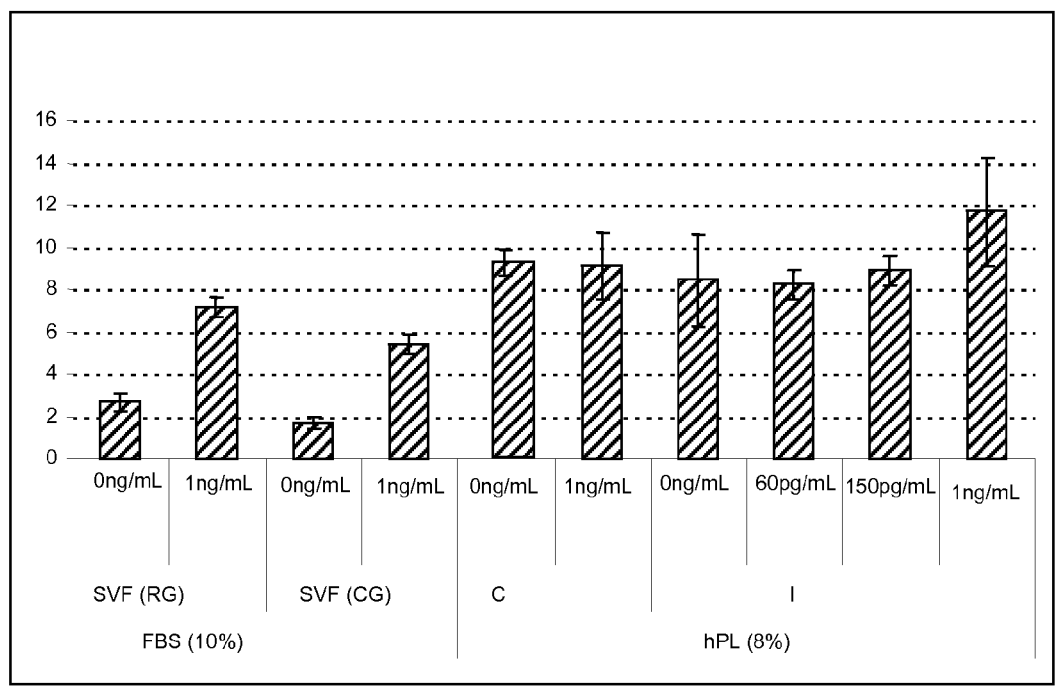
FIG. 3 represents the mean amplification rates of mesenchymal stem cells cultured in the presence of non-irradiated platelet lysates (C), platelet lysates sterilised in the frozen state with gamma irradiation at 35 kGy, platelet lysates sterilised in the frozen state with gamma irradiation at 45 kGy and foetal bovine serum (SVF (RG) and SVF (CG)), with variable concentrations of added exogenous bFGF.

FIG. 3 shows the mean of the amplification rates obtained. The results confirm the effect of bFGF in cultures in foetal bovine serum, and the absence of an effect of exogenous bFGF in cultures in non-irradiated platelet lysate.

On the other hand, by adding 60 pg/ml or 150 pg/ml to a platelet lysate irradiated with gamma radiation, the amplification rate once again becomes equivalent to that obtained with non-irradiated platelet lysate. In addition, adding 1 ng/ml of exogenous bFGF exhibits a superior amplification rate.

Phenotype

It was verified that the use of platelet lysate, optionally combined with exogenous bFGF, for the culture of mesenchymal stem cells, does not modify the expression profile of these cells, the latter remaining positive for the markers CD13, CD44, CD73, CD90 and CD105 and negative for the markers CD34, CD45 and HLA-DR. The cells are also negative for the markers CD40, CD80 and CD86.

The invention claimed is:

1. A method for sterilizing a platelet lysate comprising:
 a. providing a liquid platelet lysate;
 b. freezing said liquid platelet lysate in order to obtain a frozen platelet lysate;
 c. irradiating said frozen platelet lysate in a non freeze-dried state with gamma radiation at an absorbed dose within the range from 35-60kGy to obtain a sterilized platelet lysate, said irradiation being adapted so as to preserve at least 80% of the concentration of at least one of the endogenous growth factors chosen from the group consisting of TGF-beta1, EGF, PDGF-AB, IGF-1, and VEGF.

2. The method of claim 1, wherein the liquid platelet lysate is created from a platelet suspension.

3. The method of claim 2, wherein the creation of the liquid platelet lysate from platelet suspension comprises:
 a. subjecting the platelet suspension to at least one freezing/thawing cycle so as to obtain a platelet lysate composition;
 b. separating said platelet lysate composition into a clear platelet lysate fraction and a cellular debris fraction; and
 c. isolating said platelet lysate fraction in the liquid step to create a liquid platelet lysate.

4. The method of claim 2, wherein said platelet suspension comprises platelets suspended in plasma.

5. The method according to claim 1, further comprising a step of filtering the liquid platelet lysate through a filter of 0.22 to 0.65 µm before freezing.

6. The method according to claim 1, wherein the freezing of the liquid platelet lysate is carried out at a temperature of approximately −80° C.

7. A method for sterilizing a platelet lysate comprising:
 a. subjecting a platelet suspension to at least one freezing/thawing cycle so as to obtain a platelet lysate composition;
 b. separating said platelet lysate composition into a clear platelet lysate fraction and a cellular debris fraction; and
 c. isolating said platelet lysate fraction in the liquid step to create a liquid platelet lysate;
 d. freezing said liquid platelet lysate in order to obtain a frozen platelet lysate;
 e. irradiating said frozen platelet lysate in a non freeze-dried state with gamma radiation at an absorbed dose within the range from 35-60kGy to obtain a sterilized platelet lysate, said irradiation being adapted so as to preserve at least 80% of the concentration of at least one of the endogenous growth factors chosen from the group consisting of TGF-beta1, EGF, PDGF-AB, IGF-1, and VEGF.

* * * * *